United States Patent [19]
Lussier

[11] Patent Number: 5,945,540
[45] Date of Patent: Aug. 31, 1999

[54] SYNTHESIS OF CERTAIN PYRAZOLO-[1,5-A] BENZIMIDAZOLE COMPOUNDS

[75] Inventor: Barbara B. Lussier, Rochester, N.Y.

[73] Assignee: Eastman Kodak Company, Rochester, N.Y.

[21] Appl. No.: 09/134,311

[22] Filed: Aug. 14, 1998

[51] Int. Cl.[6] .................................................. C07D 235/02
[52] U.S. Cl. ...................... 548/302.1; 548/210; 548/213; 548/226; 548/255; 548/263.4
[58] Field of Search ........................................... 548/302.1

[56] References Cited

U.S. PATENT DOCUMENTS

| 3,079,255 | 2/1963 | Wahl et al. | 96/55 |
| 4,076,533 | 2/1978 | Ota et al. | 96/56.5 |
| 4,198,235 | 4/1980 | Vetter et al. | 430/222 |
| 4,241,168 | 12/1980 | Arai et al. | 430/503 |
| 5,143,821 | 9/1992 | Crawley et al. | 430/558 |

FOREIGN PATENT DOCUMENTS

| 1070030 | 5/1960 | Germany. | |
| 91/14970 | 10/1991 | WIPO. | |
| 97/35551 | 10/1997 | WIPO | A61K 7/13 |

OTHER PUBLICATIONS

Wahl et al., Chemical Abstract 56:10333, vol. 56, No. 9, Apr. 30, 1962.

*Primary Examiner*—Laura L. Stockton
*Attorney, Agent, or Firm*—Arthur E. Kluegel

[57] ABSTRACT

Disclosed is a process that provides steps for synthesizing intermediates useful for appending a N heterocyclic compound to the 3-position of a 4-H-pyrazolo-[1,5-a] benzimidazole compound and further steps that together provide a combined process that yields the target compounds in good yields while using readily available reagents and mild conditions.

23 Claims, No Drawings

SYNTHESIS OF CERTAIN PYRAZOLO-[1,5-A] BENZIMIDAZOLE COMPOUNDS

FIELD OF THE INVENTION

This invention relates to the synthesis of intermediates and certain 4-H-pyrazolo-[1,5-a]benzimidazole end-products bearing in the 3-position an azole group bonded through a nitrogen atom of the azole.

BACKGROUND OF THE INVENTION

Silver halide color photography depends on the formation of dyes in order to reproduce an image. These dyes are typically formed from couplers present in or adjacent to the light sensitive silver halide emulsion layers that react to image light upon exposure. During development, the latent image recorded by the silver halide emulsion is developed to amplify the image. During this process in which silver halide is reduced to elemental silver, the color developer compound used is at the same time oxidized, as is typical in a redox reaction. The oxidized developer then reacts or couples with the coupler compound present in or adjacent to the emulsion layer to form a dye of the desired color.

Typically, a silver halide emulsion layer containing a magenta dye-forming coupler is sensitized to green light. This facilitates so-called negative-positive processing in which the image is initially captured in a negative format where black is captured as white, white as black, and the colors as their complimentary colors (e.g., green as magenta, blue as yellow, and red as cyan). Then the initial image can be optically printed in the correct colors through the device of optical printing which has the effect of producing a negative of the negative, or a positive image of the original scene.

For incorporation into a photographic element, the couplers are typically dissolved in high-boiling organic solvents known as "coupler solvents," and dispersed in gelatin with the aid of surfactants.

The present invention is concerned with the preparation of 4H-pyrazolo[1,5-a]benzimidazole compounds useful as magenta dye-forming couplers (hereinafter referred to as "PBI" compounds or couplers). These compounds may broadly be described by Formula (A)

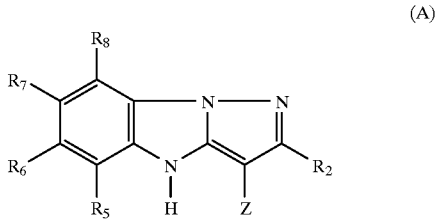

(A)

in which $R_2$ and $R_5$-$R_8$ represent substituents and Z represents a hydrogen atom or a group capable of being split off during the coupling reaction. German patent 1,070,030 discloses PBI couplers that form magenta dyes upon coupling. In the examples given, $R_2$ represents an alkyl or phenyl group. Couplers of these types have been found to have poor coupling reactivity, to yield image dyes whose absorption spectra are too bathochromic for practical use in color photographic papers, and to have poor stability to light. International Patent Application WO 91/14970 describes PBI couplers with specifically substituted alkylthio coupling-off groups, including carboxyalkylthio groups. Such couplers offer marked improvements in coupling reactivity but do not offer improved dye hue or light stability. U.S. Pat. No. 5,143,821 describes PBI couplers in which $R_2$ represents an alkoxy group. Such couplers are advantageous because they have much better coupling reactivity than those in which $R_2$ represents an alkyl group, and the image dyes formed from them have good spectral absorption characteristics. Moreover, the dyes from these couplers have better light stability than the dyes from PBI couplers in which $R_2$ is an alkyl group. However, the tendency to yellow of these alkoxy PBI couplers is unacceptable for the formation of accurate image reproductions, especially for color photographic papers.

U.S. Pat. Nos. 4,241,168 and 4,076,533 suggest the possible use of azole coupling-off groups on magenta couplers. As these patents teach, the standard procedure for introducing the N heterocycles typically involves halogenation of the coupling site followed by displacement with the N-heterocycle. Unfortunately, in the case of the PBI compounds, the halogen derivatives are unreactive toward nitrogen heterocycles at room temperature. Heating the reaction results in the thermal disproportionation of the halogen derivative that renders the yield of the desired product unsatisfactory. The use of a stabilizer such as β-hydroxytoluene (BHT), does not appear to inhibit this disproportionation, and thus this route is unfeasible.

It is a problem to be solved to provide a step for synthesizing intermediates useful for appending a N heterocyclic compound to the 3-position of a 4-H-pyrazolo-[1,5-a]benzimidazole compound and a combined process that yields the target compounds in good yields while using inexpensive reagents and mild conditions.

SUMMARY OF THE INVENTION

The invention provides a process for the nitrosation of a 4-H-pyrazolo-[1,5-a]benzimidazole ("PBI") compound in which the PBI compound is contacted with a nitrosating reagent in the presence of an inert solvent.

The invention provides steps for synthesizing intermediates useful for appending a N heterocyclic compound to the 3-position of a 4-H-pyrazolo-[1,5-a]benzimidazole compound and further steps that together provide a combined process that yields the target compounds in good yields while using inexpensive reagents and mild conditions.

DETAILED DESCRIPTION OF THE INVENTION

The invention provides a process for the nitrosation of a 4-H-pyrazolo-[1,5-a]benzimidazole ("PBI") compound in which the PBI compound is contacted with a nitrosating reagent such as nitrous acid or an alkyl nitrite in the presence of an inert solvent. The overall combined process involves the nitrosation of the parent, 4-equivalent coupler, followed by reduction to the amine, and then reaction of the resulting product with a bifunctional reagent which can cyclize back onto the nitrogen to form a heterocycle. Many compounds that contain heterocyclic azole derivatives, such as succinimide, hydantoin, urazoles, and oxazolidinedione groups can be prepared in this manner.

The nitrosation results in a nitroso compound. Such compounds are well-known to exist in the tautomeric form of an oxime compound. It is understood that such oxime compounds are intended to be included within the nitroso compounds herein.

The nitrosation reaction may be carried out as described, for example, in the texts *Advanced Organic Chemistry; Reactions, Mechanisms, and Structure* by March (J. Wiley & Sons, NY, N.Y., (1992)); *Comprehensive Organic Transformations* by LaRock (VCH Publishers, NY, N.Y. (1989)); or Nitrosation by Williams (Cambridge Univ. Press, London, (1988)). Such reactions are typically carried out using a nitrosating agent such as nitrous acid or an alkylnitirite. The former may be formed in situ by the addition of an alkali metal nitrite and a mineral acid such as HCl. Examples or suitable acid agents include sodium, potassium and ammonium nitrite and a mineral acid such as HCl. When the alkyl nitrite is used, it is a typically a liquid alkyl nitrite such as one having up to 8 carbon atoms including methyl, ethyl, propyl, i-propyl, butyl, t-butyl, pentyl, i-amyl, and the like.

The reaction may be carried out at a temperature of from −20 to 100° C. When nitrous acid is used, a temperature in the range of −20 to 50° C. and suitably 0 to 10° C. is employed. When the alkyl nitrite is used, a temperature in the range of 0 to 100° C. and typically in the range of 10–80° C. is convenient.

The inert solvents useful for the nitrosation reaction are those that can serve as a reaction medium without reacting with the intended reactants. The following solvents are examples of those useful in the nitrosation reaction: water, acetic acid, diethyl ether, tetrahydrofuran, dimethylformamide, ligroin, benzene, toluene, dichloromethane, chloroform and alcohols such as methanol, ethanol, propanol, and butanol. Ketones are reactive and not suitable. The reaction may be carried out under acidic, neutral or basic conditions. Other reaction conditions as described for nitrosation reactions in the afore-mentioned texts may be employed.

Particularly suitable are water and those solvents that are miscible with water such as the alcohols and acetic acid. The combination of methanol and water is conveniently employed.

The compound resulting from the nitrosation reaction may be represented by the formula:

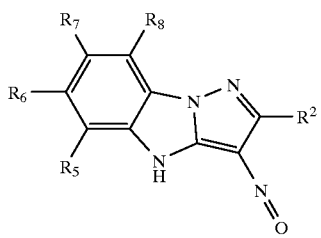

wherein

R$_2$, is a substituent; and

R$_5$, R$_6$, R$_7$, and R$_8$ are independently a hydrogen atom or a substituent.

The reduction step may be any of those taught in the art for the reduction of the nitroso (or oxime) group to the amine. See the above March and LaRock tests. Conveniently, this step is accomplished by hydrogenation of the double bond using a palladium or similar catalyst.

The further step serves to append the N hetero group to the coupler parent group. It employs a bifunctional reagent that performs the function of forming a carbon-nitrogen bond with the newly formed amine and then permitting ring closure. These bifunctional reagents contain either two electrophilic carbon centers or one electrophilic carbon center and a precursor having the ability to form a second such center by reaction. Such groups include esters, lactones, ketones, aldehydes, carboxylic acids, imino esters, hemiacetals, hemiaminals, hydrazones, enamines, electron poor alkynes and alkenes, β-ketoesters, carbonyl halides, carbamoyl halides, nitriles, imines, acetals, aminals, carbamates, iminoethers, etc. The reagent typically contains two such electrophilic carbon centered moieties. These centers are separated by a 2-atom unit so that the newly formed amine reacts either concertedly or sequentially with each of them to form the desired 5-membered azole ring. β-ketocarbonyl compounds and their precursors are useful for this purpose.

As indicated, the term "bifunctional" also includes a compound that contains only one electrophilic carbon center where there is present a second precursor group capable of being transformed into an electrophilic center after the first carbon-nitrogen bond has been formed. An example is an electrophilic carbon center compound also having an amine derivative or a protected group where the second electrophilic center can either be formed or deprotected during the reaction.

The reagents useful as bifunctional reagents include: succinimides, succinic anhydride, oxalacetyl chloride, oxalacetic acid or phthalimide; hydantoins, glycine-N-chlororcarbonyl-ethyl ester, ethyl ureidoacetate, p-nitrophenylcarbobenzoylalanine t-BOC glycine, glycine, N-(methoxycarbonyl)-methyl ester; oxazolidines such as acetic acid, [(chlorocarbonyloxy]-methyl ester; propanoic acid, 2-[(chlorocarbonyl)oxy]-methyl ester; propanoic acid, methyl-2([chlorocarbonyl)oxy]-2-methyl propanoate; urazoles, 3-(dimethylamino) acrolein and 3-(dimethyl amino)-1-phenylprop-2-ene-1-one; and benzoylacetone, 4-phenyl-3-butyne-2-one, 3-(dimethylamino)acrolein, and 3-(dimethylamino)-1-phenylprop-2-en-1-one.

Where it is desired to append a pyrazole group, after the reduction step a second amine group is appended using for example hydroxylamine-O-sulfonic acid.

Precursors for the hydantoins can readily be prepared via reaction of triphosgene with an amino acid ester.

The invention provides a process for appending an azole to a —CH-containing compound comprising reacting the compound with a bifunctional reagent containing two electrophilic centers separated by a two atom unit, or the precursors thereof, that forms a compound having an azole linked by a nitrogen atom of the azole. In one embodiment, the precursor is a primary amine.

The final step of the reaction is the closure of the azole ring that may be accomplished using known techniques from the above texts such as by a condensation reaction.

The reactions and intermediates of the invention are represented in the following schemes:

Synthesis of Heterocyclic Coupling-off Groups

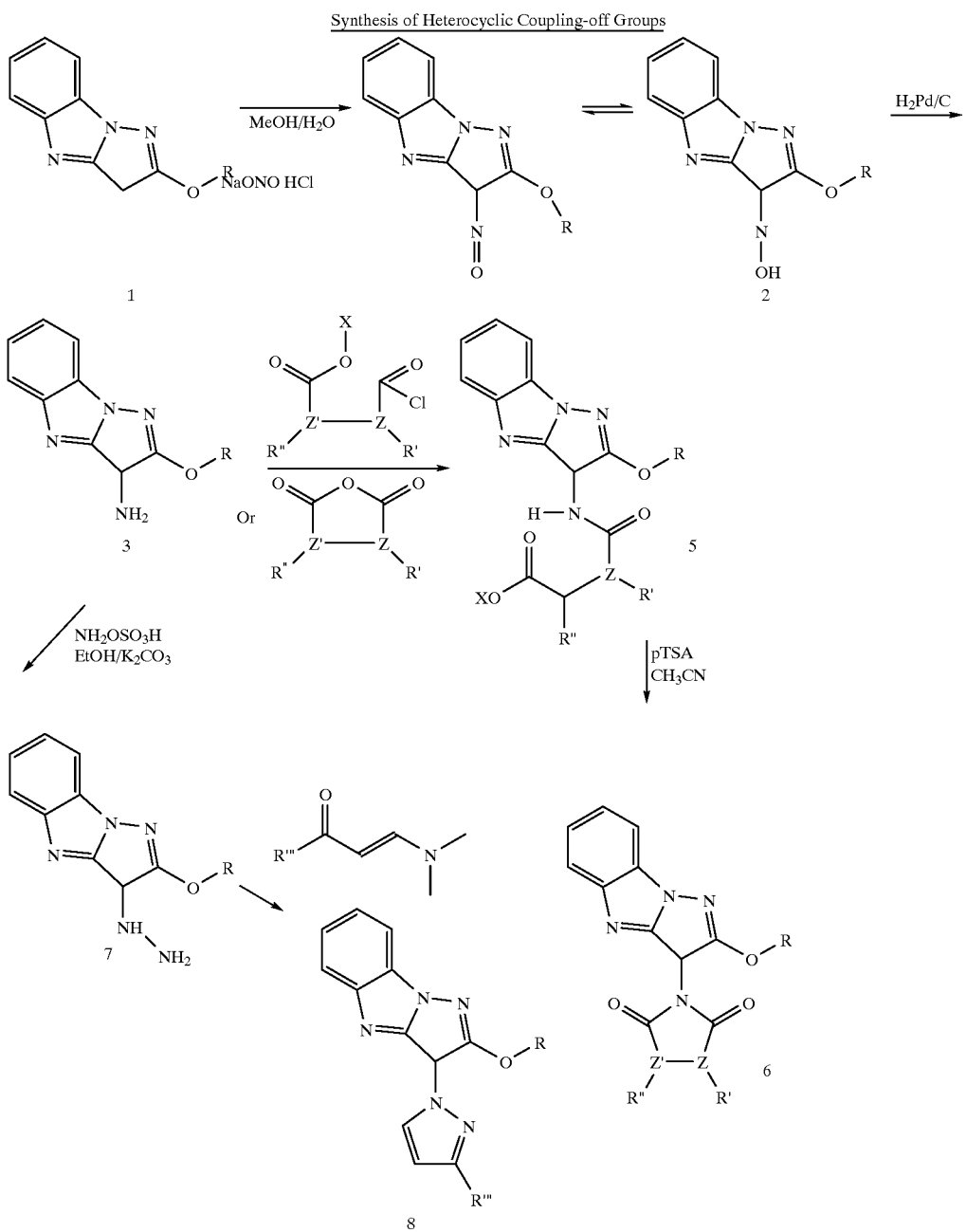

In the schemes, Me is methyl, Et is ethyl, pTSA is para-touenesulfonic acid, the various Z groups represent carbon or heteroatoms such as O, S, or N and the R' and R" groups represent possible substituents which may be possible depending on the Z groups selected.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, 1-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)]butylcarbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The following are specific examples of magenta couplers that can be synthesized in accordance with the invention:

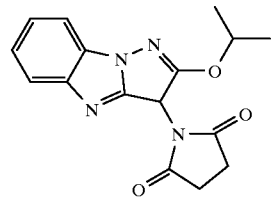

MC1

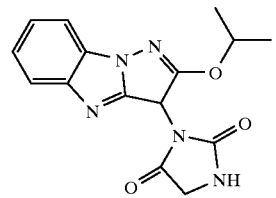

MC2

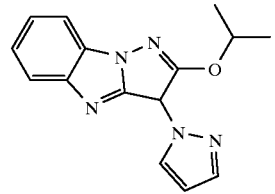

MC3

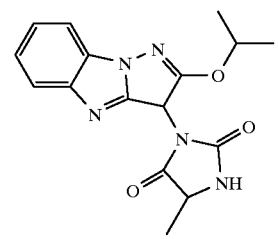

MC4

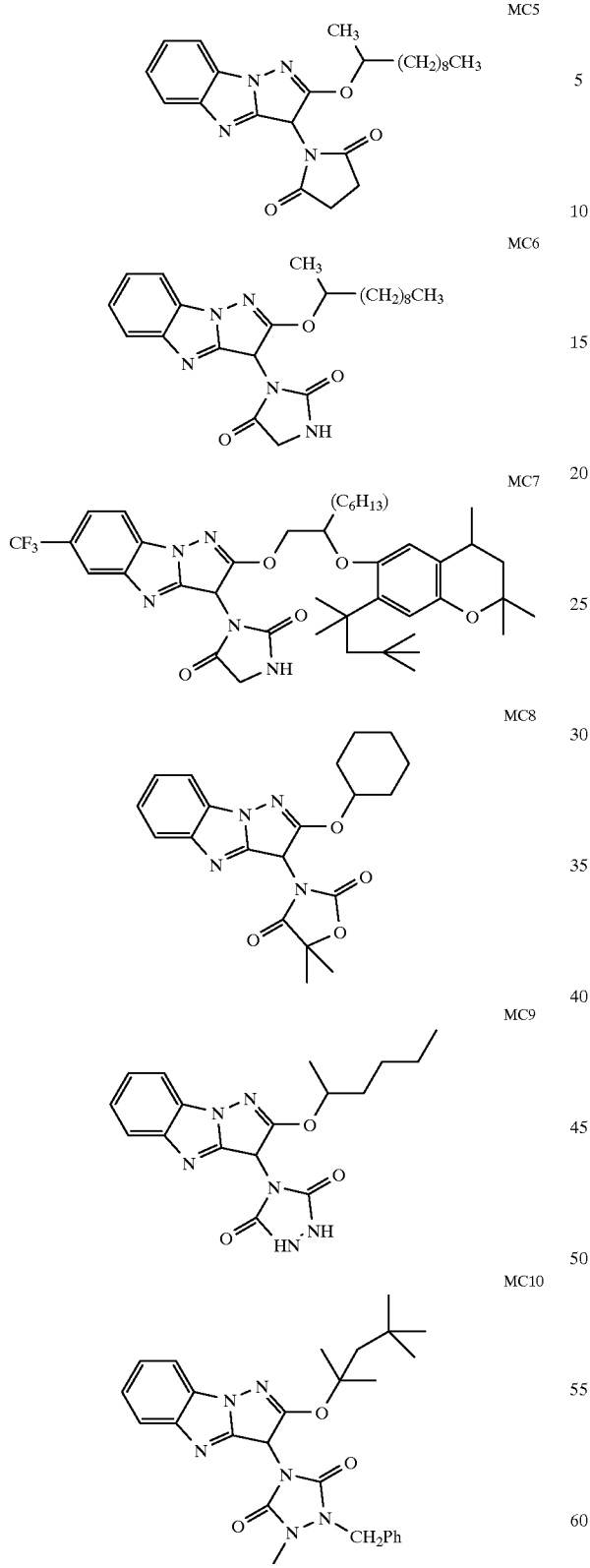
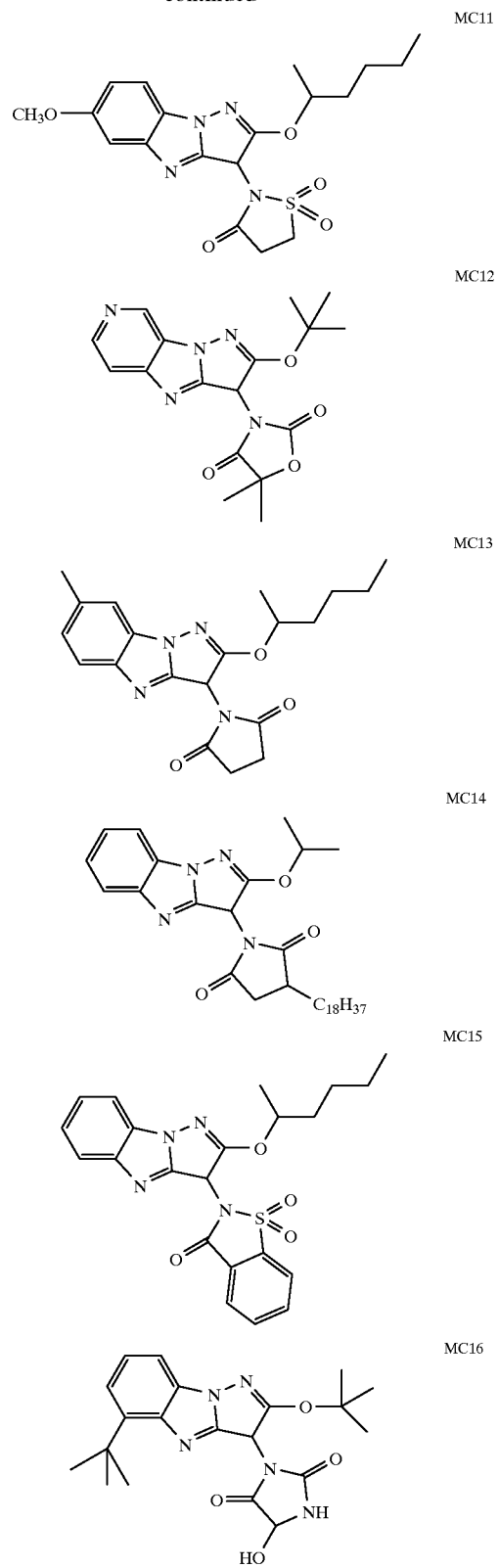

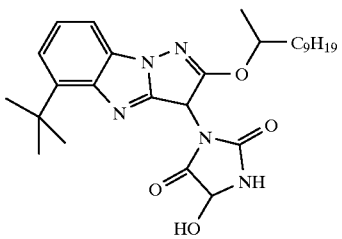

MC17

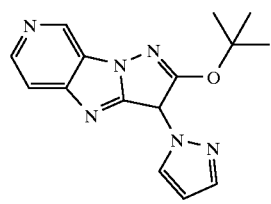

MC18

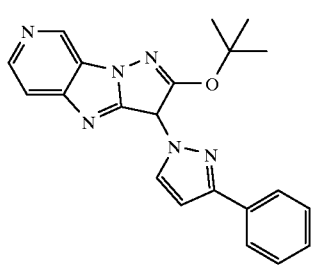

MC19

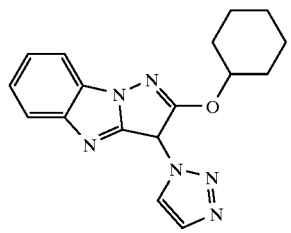

MC20

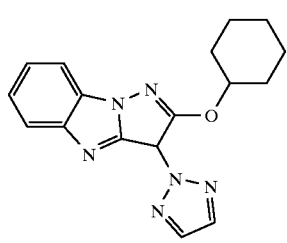

MC21

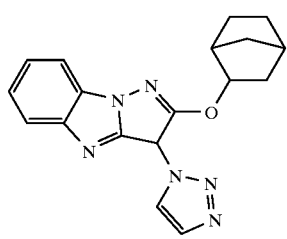

MC22

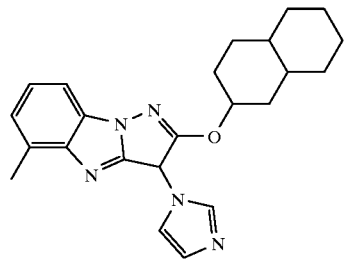

MC23

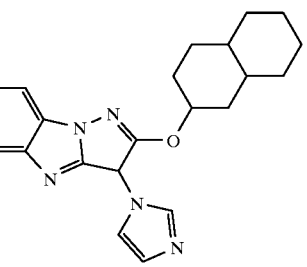

SYNTHESIS EXAMPLES

Preparation Of Coupler MC-1

Compound 1(R=isopropyl) (6.24 g, 0.029 mol) was dissolved in a mixture of methanol (50 mL) and water (50 ml). The mixture was cooled in an ice bath. Concentrated HCl (3.0 mL) was added. A solution of sodium nitrite (2.2 g, 0.032 mol) in water (10 mL) was added dropwise. The mixture was allowed to stir for 1 hour. The ice bath was removed and the reaction mixture was poured into 500 ml. water. The orange precipitate was filtered and washed well with water. Drying under vacuum yielded 6.9 g of compound 2(R=isopropyl), suitably pure for further use.

Compound 2(R=isopropyl) (4.0 g, 0.016 mol) was dissolved in ethanol (150 ml) in a Parr bottle and heated to effect solution. 5% Pd/C catalyst (0.4 g) and succinic anhydride (2.0 g, 0.02 mol) were added. The vessel was shaken under hydrogen (50 psi) for 8 hours. The catalyst was filtered off and the filtrate stripped of solvent to yield a quantitative conversion to compound 5(R=isopropyl; Z', Z"=CH; R', R"=H, X=H).

Compound 5(R=isopropyl; Z', Z"=CH; R', R"=H, X=H) (4.0 g, 0.012 mol) was dissolved in acetonitrile (100 mL) and p-toluenesulfonic acid (0.1 g) added. The solution was heated to reflux for 4 hours. The solvent was removed in vacuo and the residue recrystallized from ligroin/diethyl ether to yield 3.0 g of MC-1. Mass spectra: FDMS 312.

1H nmr (CDCl$_3$): δ 1.4, (m, 6H), 2.8 (s, 4H), 5.1 (m, 1H), 7.0–7.5 (m, 4H), 8.7 (s, 1H).

Preparation of Coupler MC-6

Compound 1(R=2-undecyl) (10.0 g, 0.03 mol) was dissolved in a mixture of methanol (50 ml) and water (50 ml). The mixture was cooled in an ice bath. Concentrated HCl (3.2 mL) was added. A solution of sodium nitrite (2.3 g, 0.034 mol) in water (10 ml) was added dropwise. The mixture was allowed to stir for 1 hour. The ice bath was removed and the reaction mixture was poured into 500 ml water. The orange precipitate was filtered and washed well with water. Drying under vacuum yielded 10.7 g of compound 2(R=2-undecyl), suitably pure for further use.

Compound 2(R=undecyl) (5.0 g, 0.014 mol) was dissolved in ethyl acetate (150 ml), in a Parr bottle and heated to effect solution. 5% Pd/C catalyst (0.4 g), was added. The vessel was shaken under hydrogen (50 psi) for 8 hours. The catalyst was filtered off and the filtrate added to a solution of glycine, N-(chlorocarbonyl)ethyl ester (2.31 g, 0.014 mol) in dichloromethane (25 ml). An aliquot of diethylisopropylamine was added dropwise. The mixture stirred for 3 hours at room temperature. It was then submitted to aqueous, acidic workup and extraction with ethyl acetate. Upon removal of the solvent, white crystals formed which were filtered to yield compound 5(R=2-undecyl, Z=N, Z'=CH, R', R"=H, X=C$_2$H$_5$).

Compound 5(R=2-undecyl, Z=N, Z'=CH, R', R"=H, X=C$_2$H$_5$), (3.2 g, 0.0068 mol) was dissolved in toluene (100 ml) and p-toluenesulfonic acid (0.1 g) added. The solution was heated to reflux for 4 hours. The solvent was removed in vacuo and the residue recrystallized from ligroin/diethyl ether to yield 3.0 g of MC-6. Mass spectra: FDMS 425.

1H nmr (CDCl$_3$): δ 6 0.8 (q, 3H), 1.4–1.9 (m, 19H), 4.4 (2H), 4.9 (m, 1H), 6.8–7.2 (m, 4H), 7.8 (s, 1H).

What is claimed is:

1. A process for the nitrosation of a 4-H-pyrazolo-[1,5-a] benzimidazole ("PBI") compound that may be substituted with halogen; nitro; hydroxyl; cyano; carboxyl; or alkyl, alkenyl, alkoxy, aryl, aryloxy, carbonamido, sulfonamido, sulfamoyl, carbamoyl, acyl, sulfonyl, sulfonyloxy, sulfinyl, thio, acyloxy, amine, imino, phosphate, phosphite, a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, quaternary ammonium, and silyloxy, which substituents may themselves be further substituted one or more times with the described substituent groups comprising reacting the PBI compound with a nitrosating reagent in the presence of an inert solvent.

2. The process of claim 1 wherein the inert solvent includes water or a water miscible solvent.

3. The process of claim 2 wherein the solvent includes water.

4. The process of claim 2 wherein the solvent includes a water miscible solvent selected from the group consisting of alcohols and acetic acid.

5. The process of claim 4 wherein the solvent is selected from methanol, ethanol, propanol, and butanol.

6. The process of claim 2 wherein the solvent comprises methanol and water.

7. The process of claim 1 wherein the nitrosating agent is nitrous acid.

8. The process of claim 7 wherein the nitrous acid results from the addition of an alkali metal or ammonium nitrite and a mineral acid.

9. The process of claim 8 wherein the mineral acid is HCl.

10. The process of claim 1 wherein the nitrosating agent is an alkyl nitrite.

11. The process of claim 10 wherein the alkyl group of the alkyl nitrite contains up to 8 carbon atoms.

12. The process of claim 1 wherein the temperature of the reaction is in the range of about −20 to 100° C.

13. The process of claim 7 wherein the temperature of the reaction is in the range of about −20 to 50° C.

14. The process of claim 13 wherein the temperature is maintained in the range of about 0 to 10° C.

15. The process of claim 10 wherein the temperature of the reaction is in the range of about 0 to 100° C.

16. The process of claim 15 wherein the temperature is maintained in the range of about 10 to 80° C.

17. The process of claim 1 comprising the additional subsequent step of subjecting the product of claim 1 to a reduction reaction to form a 3-amino-PBI compound.

18. The process of claim 17 in which the subsequent step includes hydrogenation in the presence of a catalyst.

19. The process of claim 17 comprising the still later subsequent step of reacting the product of claim 17 with a bifunctional reagent, containing two electrophilic centers separated by a two atom unit, or the precursors thereof, that forms a compound of formula I having an azole in the 3-position linked by a nitrogen atom of the azole:

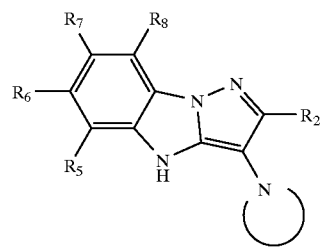

wherein:

R$_2$ is a substituent;

R$_5$, R$_6$, R$_7$, and R$_8$ are each independently a hydrogen atom or a substituent;

represents the atoms necessary to complete a five-membered ring containing from 1 to 3 nitrogen atoms.

20. The process of claim 19 wherein the bifunctional reagent is selected from the group consisting of succinimides, hydantoins, oxazolidines, urazoles, and pyrazoles.

21. The process of claim 19 wherein R$_2$ is an alkyl or alkoxy group.

22. The process of claim 1 wherein the PBI reactant compound is represented by Formula (A)

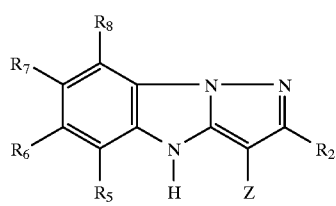

in which R$_2$ and R$_5$–R$_8$ represent substituents and Z represents a hydrogen atom.

23. A compound represented by the formula:

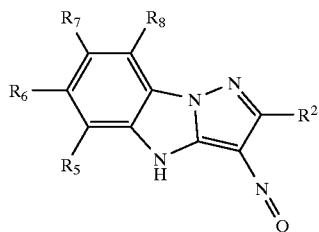

wherein:

$R_2$ is a substituent; and $R_5$, $R_6$, $R_7$, and $R_8$ are each independently a hydrogen atom or a substituent; where the substituent are selected from halogen nitro; hydroxyl; cyano; carboxyl; or alkyl, alkenyl, alkoxy, aryl, aryloxy, carbonamido, sulfonamido, sulfamoyl, carbamoyl, acyl, sulfonyl, sulfonyloxy, sulfinyl, thio, acyloxy, amine, imino, phosphate, phosphite, a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, quaternary ammonium, and silyloxy, which substituents may themselves be further substituted one or more times with the described substituent groups.

* * * * *